United States Patent
Shields et al.

(10) Patent No.: US 10,420,873 B2
(45) Date of Patent: Sep. 24, 2019

(54) DEVICE FOR FORMING FISTULA BETWEEN BLOOD VESSELS, AND METHOD

(71) Applicant: Cook Medical Technologies LLC, Bloomington, IN (US)

(72) Inventors: Adam Shields, Lafayette, IN (US); Keith Milner, West Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 509 days.

(21) Appl. No.: 14/668,049

(22) Filed: Mar. 25, 2015

(65) Prior Publication Data

US 2015/0352273 A1     Dec. 10, 2015

Related U.S. Application Data

(60) Provisional application No. 62/008,818, filed on Jun. 6, 2014.

(51) Int. Cl.
*A61M 1/36* (2006.01)
*A61B 17/11* (2006.01)

(52) U.S. Cl.
CPC .......... *A61M 1/3655* (2013.01); *A61B 17/11* (2013.01); *A61B 2017/1107* (2013.01); *A61B 2017/1135* (2013.01)

(58) Field of Classification Search
CPC . A61B 17/11; A61B 17/064; A61B 17/12009; A61B 2017/1107; A61B 2017/1135; A61M 27/002; A61M 39/10; A61F 2/06

USPC .................................................. 604/6.16, 8–10
See application file for complete search history.

(56) References Cited

U.S. PATENT DOCUMENTS

| | | | |
|---|---|---|---|
| 5,344,425 A | 9/1994 | Sawyer | |
| 6,019,788 A * | 2/2000 | Butters | ............... A61B 17/064 604/8 |
| 6,616,675 B1 | 9/2003 | Evard et al. | |
| 7,128,750 B1 | 10/2006 | Stergiopulos | |
| 7,331,989 B2 | 2/2008 | Houston et al. | |
| 7,682,673 B2 * | 3/2010 | Houston | ................... A61F 2/06 428/35.8 |
| 8,382,697 B2 | 2/2013 | Brenneman et al. | |
| 8,523,800 B2 | 9/2013 | Brenneman et al. | |
| 2009/0036817 A1 * | 2/2009 | Dakin | .................... A61B 17/11 604/8 |
| 2012/0123520 A1 | 5/2012 | Houston et al. | |
| 2013/0110029 A1 | 5/2013 | Dakin et al. | |
| 2013/0310808 A1 | 11/2013 | Stout et al. | |

FOREIGN PATENT DOCUMENTS

| | | |
|---|---|---|
| EP | 2136734 | 10/2008 |
| WO | 9844869 | 10/1998 |
| WO | 2014026146 A | 2/2014 |

* cited by examiner

*Primary Examiner* — Philip R Wiest
(74) *Attorney, Agent, or Firm* — Liell & McNeil

(57) ABSTRACT

A device for forming a fistula between blood vessels includes a tubular body having a central lumen, a flange attached to the tubular body and projecting outwardly from an outer body surface, and one or more vanes projecting inwardly into the lumen so as to induce helical flow in blood passed through the lumen between first and second vessels joined via the fistula.

1 Claim, 4 Drawing Sheets

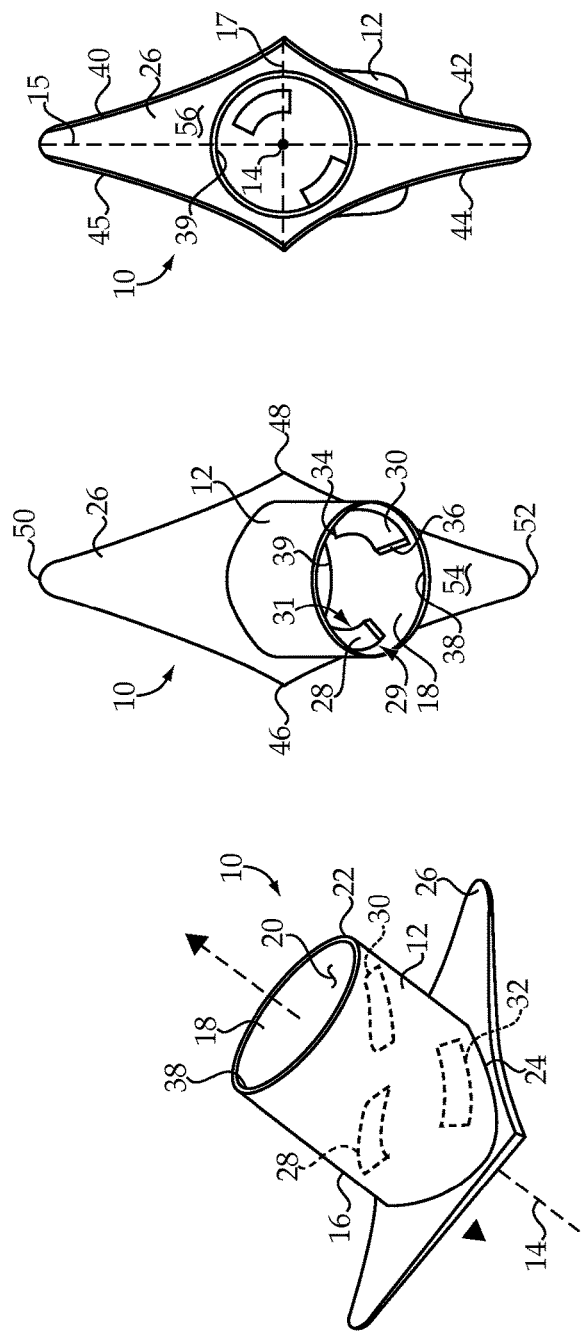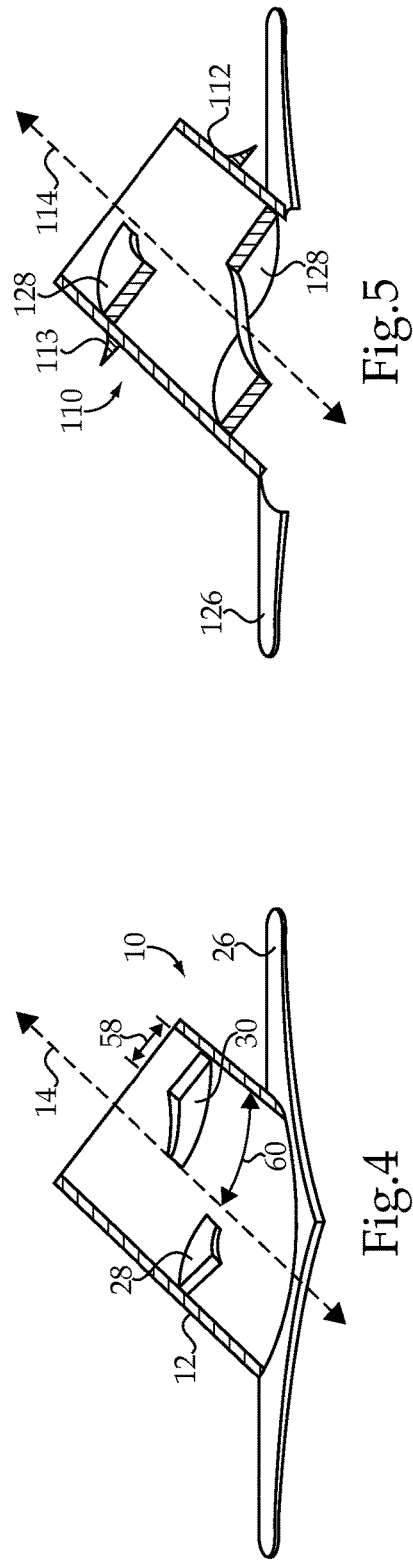

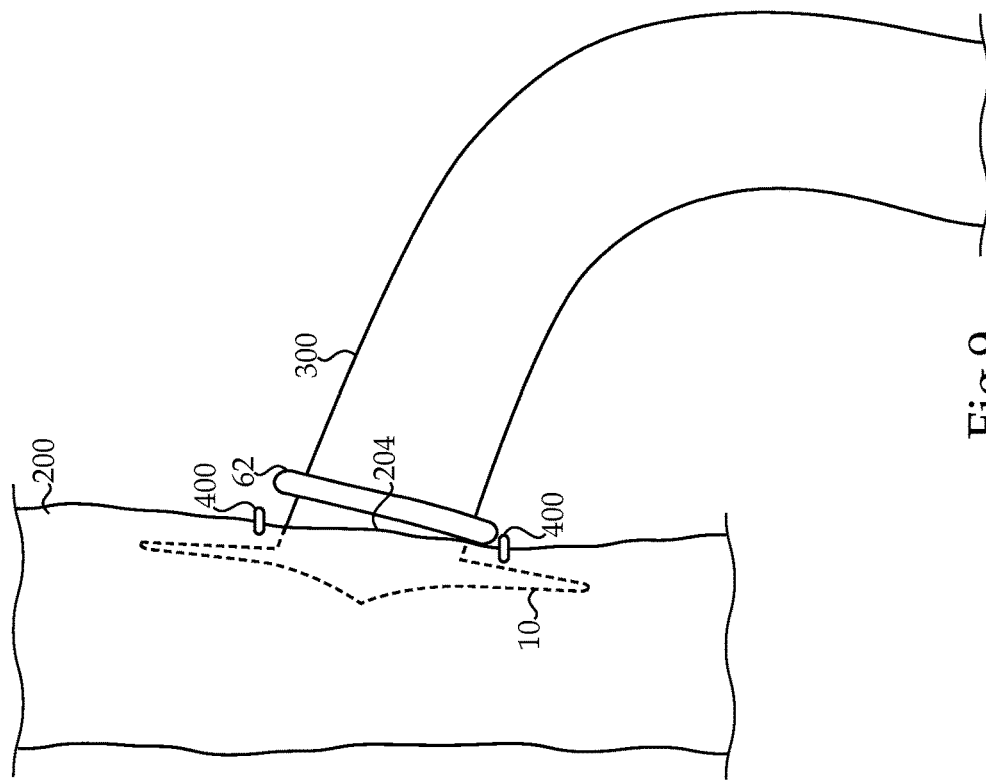
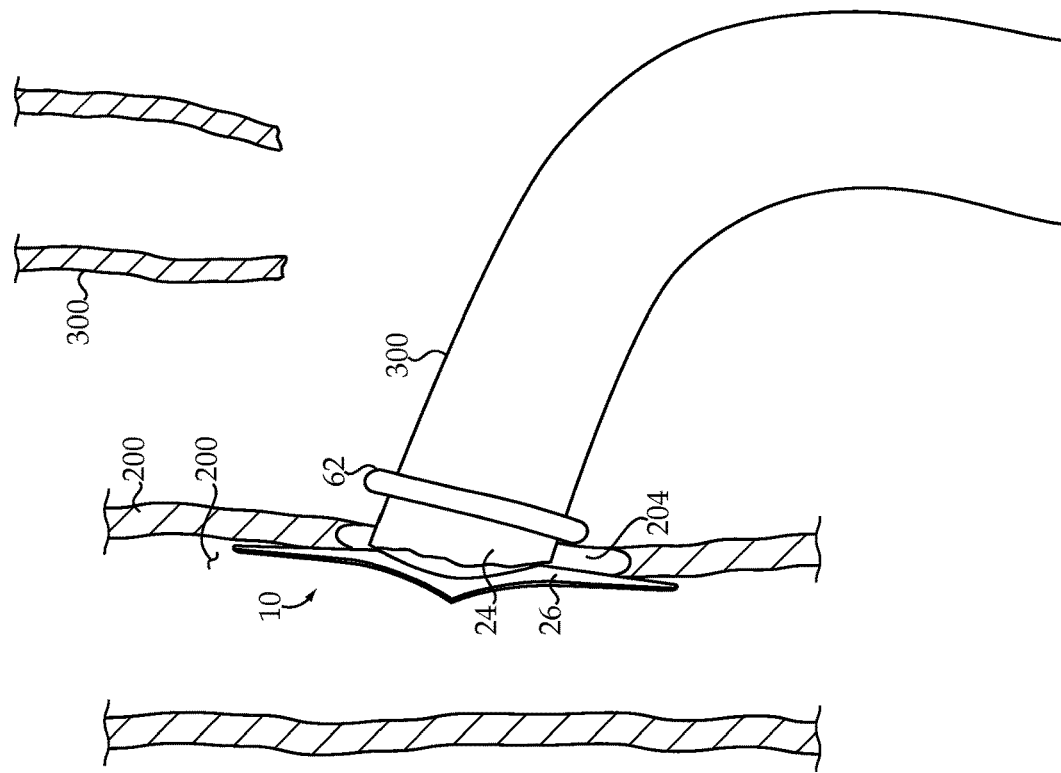

DEVICE FOR FORMING FISTULA BETWEEN BLOOD VESSELS, AND METHOD

TECHNICAL FIELD

The present disclosure relates generally to forming a fistula between blood vessels, and more particularly to a device for fistula formation where a vane within a tubular body of the device induces helical flow in blood passed through the tubular body.

BACKGROUND

Renal disease is a significant health challenge in the United States and elsewhere. Lack of organ transplant availability means that most patients are treated by dialysis, with roughly ten times as many patients receiving hemodialysis versus other forms. To minimize treatment time, hemodialysis requires a relatively large blood volume flow rate typically achieved through an arteriovenous shunt created through surgery. This shunt creates a low resistance pathway that can result in significantly increased flow rate through an arteriovenous fistula. Grafts have also been widely used.

In recent years, arteriovenus fistulas have been increasingly used to the exclusion of grafts, as data has emerged demonstrating that fistulas tend to have better long term patency rates and reduced requirements for intervention. There are nevertheless various challenges associated with fistula usage. After surgical creation of an arteriovenous fistula, the inflow and outflow vessels must dilate sufficiently and the venous tissue must generally undergo a remodeling process known as fistula maturation in order to be able to sustain the high flow rates needed for dialysis. This maturation process is only successful in about sixty percent of arteriovenous fistulas.

Another common problem is tissue proliferation along the lumen of the vein know as neointimal hyperplasia or NIH. NIH may lead to stenosis, reduced flow and ultimately failure of the fistula. Abnormal flow through an arteriovenous fistula is often observed with auscultation in the nature of characteristic vibration, believed likely to stem from turbulent flow through the vasculature. Various devices and techniques for use in fistula formation have been proposed over the years. Such technologies, however, suffer from a variety of drawbacks and shortcomings as evidenced by the still relatively low success rates of fistula maturation. Moreover, some devices for fistula formation are purpose-engineered for certain specific applications and may be less well suited to others. U.S. Pat. No. 8,523,800 to Brenneman et al., contemplating a shunt rivet for implantation in the aorta and inferior vena cava, is one such example.

SUMMARY OF THE DISCLOSURE

In one aspect, a device for forming a fistula between blood vessels includes a tubular body defining a longitudinal axis and being positionable within an opening in an end of a first vessel. The tubular body includes an outer surface, an inner surface, and a central lumen extending between a first axial end and a second axial end. The device further includes a flange positionable within an opening in the side of a second vessel to be connected to the first vessel via the fistula. The flange is attached to the tubular body at the second axial end and projects outwardly from the outer surface. The device further includes at least one vane attached to the tubular body and projecting inwardly from the inner surface into the lumen. The at least one vane has an axially and circumferentially advancing orientation so as to induce helical flow in blood passed through the lumen between the first and second vessels.

In another aspect, a method of connecting blood vessels in a patient includes sliding a first end of a tubular body in a device for forming a fistula into an opening in the end of a first vessel so as to fluidly connect the first vessel with a lumen in the tubular body. The method further includes sliding a flange attached to a second end of the tubular body into an opening in the side of a second vessel so as to fluidly connect the second vessel with the lumen. The method still further includes establishing blood flow communication between the first vessel and the second vessel via the fluid connections of the first and second vessels with the lumen, and inducing helical flow in blood passed through the lumen via a vane projecting into the lumen.

BRIEF DESCRIPTION OF THE DRAWINGS

FIG. 1 is a perspective view of a device, according to one embodiment;

FIG. 2 is a top view of the device of FIG. 1;

FIG. 3 is a bottom view of the device of FIGS. 1 and 2;

FIG. 4 is a partially sectioned side diagrammatic view of the device of FIGS. 1-3;

FIG. 5 is a partially sectioned side diagrammatic view of a device according to another embodiment;

FIG. 8 is a diagrammatic view at yet another stage of the procedure;

FIG. 9 is a diagrammatic view at yet another stage of the procedure; and

DETAILED DESCRIPTION

Figure 7:
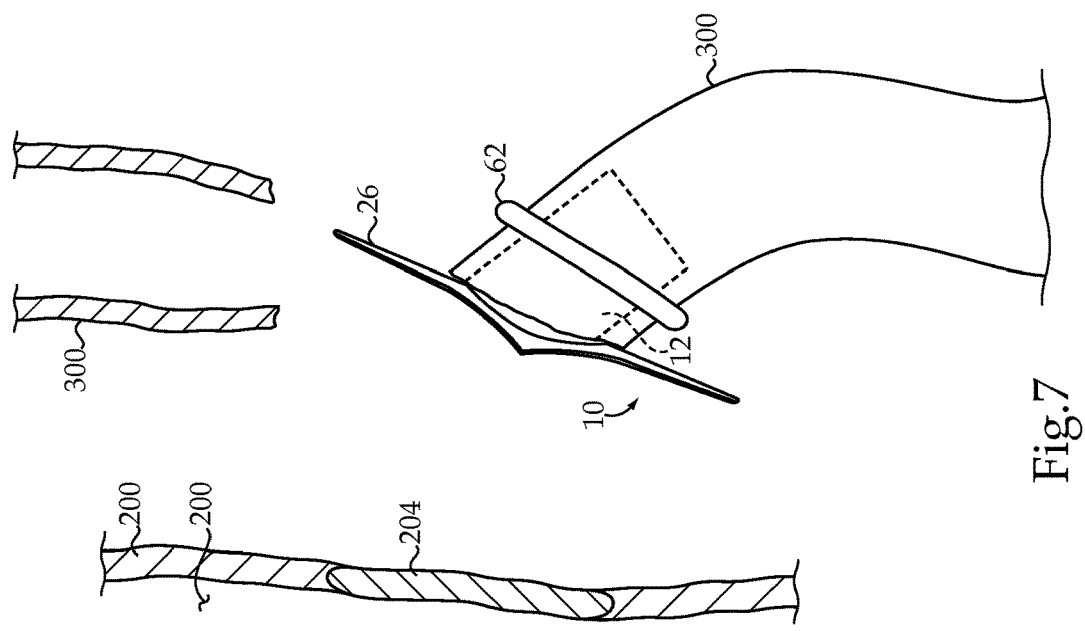
FIG. 7 is a diagrammatic view at another stage of the procedure.

Referring to FIG. 1, there is shown a device 10 for forming a fistula between blood vessels in a patient. Device 10 includes a tubular body 12 defining a longitudinal axis 14, and being positionable within an opening in the end of a first vessel. Tubular body 12 includes an outer surface 16, and an inner surface 18. A central lumen 20 extends between a first axial body end 22 and a second axial body end 24. A flange 26 is attached to tubular body 12 at second axial body end 24, and positionable within an opening in the side of a second vessel to be connected to the first vessel via the fistula. Flange 26 projects outwardly from outer surface 16. At least one vane 28 is attached to tubular body 12 and projects inwardly from inner surface 18 into lumen 20. Vane 28 has an axially and circumferentially advancing orientation so as to induce helical flow in blood passed through central lumen 20 between the first and second vessels. In a practical implementation strategy flange 26 is circumferential of tubular body 12. In other embodiments, flange 26 might extend only part way about tubular body 12, having a circumferential extent less than 360°. Device 10 may be formed as a one-piece, unitary injection molded part formed of a suitable biocompatible polymer material, but in other instances could be formed from two separately constructed pieces attached to one another by way of an adhesive or welding together of the pieces. As will be further apparent from the following description, device 10 provides an efficient mechanism for forming an arteriovenous or other fistula. Device 10 can, moreover, be expected to promote improved fistula patency through reduction in hyperplasia as a result of the induced helical flow as further discussed herein.

Referring also now to FIGS. 2, 3 and 4, tubular body 12 may be cylindrical, and flange 26 may project outwardly in directions oriented diagonally to longitudinal axis 14. Flange 26 may be elongated so as to define a minor diameter 17 and a major diameter 15. Major diameter 15 may be oriented diagonally to longitudinal axis 14. As can be seen from FIG. 3, minor diameter 17 and major diameter 15 are in the plane of the page in that illustration, and axis 14 will be understood to extend in and out of the page but at an angle corresponding generally to an orientation of tubular body 12. As can further be seen from FIG. 3, in the illustrated embodiment major diameter 15 and minor diameter 17 are oriented normal to one another and intersect one another and longitudinal axis 14 at a common point. Minor diameter 17 is oriented normal to axis 14. The diagonal orientation of tubular body 12 relative flange 26 can assist in forming a fistula inasmuch as bending and/or turning the attached vessels may be less than would be required with a design where a tubular body and flange are orthogonal to one another. An included angle between axis 14 and major diameter 15 might be from about 20 degrees to about 70 degrees, although the present disclosure is not thereby limited.

From FIG. 2 it can be seen that flange 26 has an upper side 54 oriented toward tubular body 12, and shown in FIG. 3 is a lower side 26 that faces away from tubular body 12. In a practical implementation strategy, upper side 54 may include a convex side, and lower side 56 may include a concave side. Flange 26 further includes a plurality of edges 40, 42, 44 and 45. Each of these edges may be concave, and together impart a roughly diamond shape to flange 26, facilitating insertion within a slit opening in the second vessel noted above, and as will be further apparent from the following description. Alternating with the plurality of edges, and formed at junctions of the plurality of edges, are a plurality of corners, including two sharp corners 46 and 48 and the two blunt corners 50 and 52. It will be understood that the terms "sharp" and "blunt" are used herein in a relative sense, and no part of device 10 will typically be sharp in the sense of capable of readily slicing blood vessel tissue. Blunt corners 50 and 52 can facilitate slipping device 10 into a slit opening in a vessel, as further discussed herein, whereas corners 46 and 48 can assist in retention of device 10 by way of impinging upon inner vessel walls of a blood vessel receiving flange 26. The concave and convex shapes of surfaces 54 and 56 will assist in substantially matching a shape of flange 26 to the vessel lumen wherein flange 26 is to be implanted. In other embodiments, flange 26 might have the shape of an ellipse, or still another geometry such as ovoid, circular, or irregular.

As noted above, device 10 includes at least one vane 28, shown in phantom in FIG. 1. In a practical implementation strategy, the at least one vane 28 circumferentially advances at least one complete turn about axis 14. In a further practical implementation strategy, the at least one vane 28 includes a plurality of vanes 28, 30 and 32. As also noted above, the at least one vane 28 projects inwardly from inner surface 18 into central lumen 20. Inner surface 18 may have a cylindrical shape, and an extent of inward projection of vanes 28, 30 and 32 may be from about ⅓ to about ⅔ a radial distance from inner surface 18 to axis 14. Another way to understand this feature, as best shown in FIG. 4, is that a radial extent 58 of each of the vanes from inner surface 18 in a straight line toward axis 14 is from about ⅓ to about ⅔ of the total distance from inner surface 18 to axis 14. A circumferential extent 60 of each of vanes 28, 30 and 32 about axis 14 may be such that a total or sum circumferential extent of all the vanes, as noted above, is equal to at least one full turn, or 360°, about longitudinal axis 14. In certain instances, it might be desirable to have a greater sum circumferential extent, or a lesser sum circumferential extent of the plurality of vanes.

It will regardless typically desirable to impart circumferential velocity components to blood passing between an opening 38 in first axial end 22 and an opening 39 in second axial end 34, within a relatively short axial distance. In other words, since it is generally desirable to avoid substantially obstructing flow or occluding the available flow area for blood, it will tend to be desirable to impart the helical flow relatively aggressively, and without utilizing vanes that extend a full axial length of tubular body 12 between openings 38 and 39. In FIG. 2, vane 28 is shown having an inner vane edge 31, and an outer vane edge 29 adjoining inner surface 18. Vane 30 is shown having a leading edge 34, which will typically be directed in an upstream direction respecting blood flow through device 10, and a trailing edge 36. Edges 34 and 36 might be shaped, such as being rounded, to impart desirable flow characteristics to blood, such as reducing turbulence. Orientations of edges 34 and 36 may be substantially perpendicular to inner surface 18. In certain embodiments, an unobstructed line of sight parallel to axis 15 extends through central lumen 20 between a leading edge and a trailing edge of an adjacent pair of the plurality of vanes. From FIG. 4 it can be readily seen that an unobstructed line of sight would extend between vanes 30 and 28 in the manner described. Vane 32 in FIG. 4 will be understood to be above the plane of the page, and thus not visible in the sectioned view. Alternative embodiments are contemplated, however, where the vanes have an overlapping configuration, so that no unobstructed line of site could be found between leading and trailing vane edges in the manner described.

Referring now to FIG. 5, there is shown a device 110 having certain similarities with device 10 described above, but certain differences. Device 110 includes a tubular body 112 and an attached flange 126, where tubular body 112 defines a longitudinal axis 114. Rather than a plurality of vanes, a single vane 128 is provided, and advances axially and circumferentially through tubular body 112, with the extent of axial advancement being a majority of an axial length of tubular body 112, and an extent of the circumferential advancement being greater than 360°, in the illustrated example about 1¼ turns about axis 114. Device 110 also includes a vessel retention feature 113 in the nature of a barb 113 circumferential of tubular body 112, and projecting radially outward. Those skilled in the art will appreciate analogy between the shape of barb 113 and features known from the field of connecting valve fittings to tubes. As a blood vessel to be joined to another via device 110 is slid over tubular body 112, after passing over barb 113, retention of the blood vessel in place will generally be enhanced by gripping of barb 113. Barb 113 is one example of a number of different features that might be used for retention of a blood vessel about tubular body 112. "Barb" 113 might instead be a plurality of barbs, non-circumferential barbs, or still another geometric contrivance for mechanical retention such as a plurality of spicules. In still other instances, one or more through-holes might extend through tubular body 112, or tubular body 12 by way of analogy, to enable sutures to be passed through a blood vessel and also through device 10 to secure the two together. A small hole through tubular body 112 in a generally radial direction can be readily visualized for such purposes. In still other instances, a clamp or some other external mechanism might be used, and a practical implementation strategy further discussed below includes a resilient loop such as a medical grade rubber band held in tension and positioned upon tubular body 12, such that the resilient loop can be rolled over the vessel receiving tubular body 12, 112.

In view of the foregoing, it will be readily understood that a variety of different geometries are contemplated herein respecting tubular body 12, 112, the at least one vane 28, 128, and flange 26, 126. Features described herein in connection with either of devices 10 or 110 might be employed in the same device. Both barbs or the like and a resilient rubber band could be used together. Still other alternatives to the designs specifically illustrated might include a tubular body at a shallower or a steeper angle relative to an attached flange, or a tubular body having a non-uniform inner diameter dimension, for instance flaring outwardly or inwardly away from the attached flange, depending upon the hemodynamic properties it is desirable to impart. Further still, while each of vanes 28, 30 and 32 are shown having a generally constant pitch, as is vane 128, in other embodiments the pitch of one or more vanes could vary within the corresponding tubular body. The vanes illustrated herein also have a generally consistent extent of radial projection, in other words radial width. In other embodiments, vanes could have a tapered radial extent, starting at about zero toward one axial end of the corresponding tubular body, increasing as the vane extends in an axial direction, and then decreasing once again as the vane approaches its end. Still further variations will be readily apparent to those skilled in the art.

INDUSTRIAL APPLICABILITY

Figure 6:
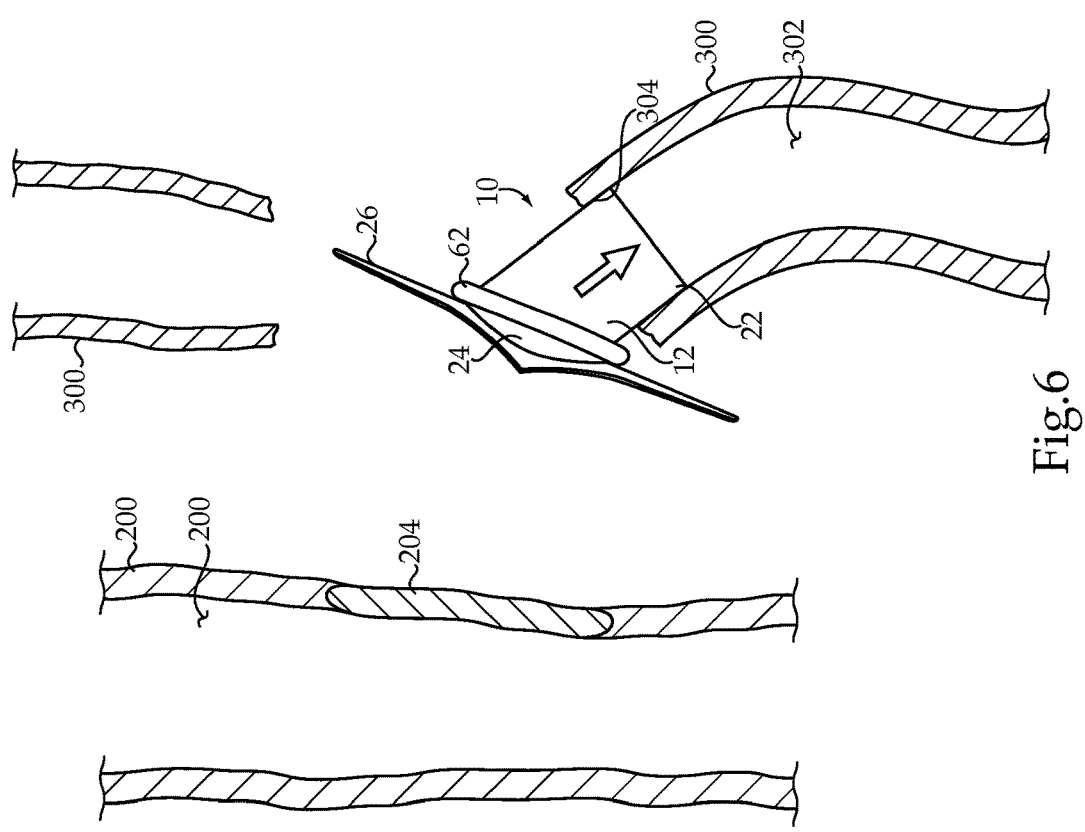
FIG. 6 is a diagrammatic view at one stage of a procedure, according to one embodiment.

Referring now to the drawings generally, but in particular to FIG. 6, there is shown a first vessel 300 having been severed, such as by a physician with a surgical cutting tool, rendering an opening 304 in the end thereof. Device 10 is shown in the process of sliding end 22 of tubular body 12 into opening 304 so as to fluidly connect first vessel 300, and in particular a vessel lumen 302, with lumen 20 in tubular body 12. The present description of the use of device 10 will be understood to refer analogously to device 110. Also shown in FIG. 6 is a resilient band 62 held in tension upon tubular body 12. The arrow upon tubular body 12 indicates an approximate direction of sliding relative to vessel 300. Also shown in FIG. 6 is a second vessel 200 having an opening 204 such as a slit formed in a side thereof.

Referring now to FIG. 7, there is shown device 10 more fully positioned within vessel 300, and where resilient band 62 has been rolled or slid over vessel 300 to retain device 10 within vessel 300. Referring also to FIG. 8, there is shown device 10 connected to vessel 300 where flange 26, attached to second end 24 has been slid into opening 204 so as to fluidly connect second vessel 200 with lumen 20 in device 10. After completely sliding flange 26 into vessel 200, blood flow communication between vessel 300 and vessel 200 may be established via the fluid connections of vessels 300 and 200 with lumen 20. Blood flow communication may be controlled via a clamp or the like about vessel 200 in a conventional manner. It can be seen from the drawings that flange 26 may be elongated, and also that a length of flange 26 may be greater than a length of opening 204. Accordingly, inserting flange 26 into opening 204 may involve deforming tissue of vessel 200 at least modestly and entering flange 26 at an angle. Sliding of flange 26 into vessel 200 in this manner might be facilitated by slipping one of corners 50 and 52 into opening 204 first, and following with the rest of flange 26 and part of tubular body 12. It will be appreciated that major diameter 15 of flange 26 may be aligned with opening 204, in other words the slit, during the insertion of flange 26.

Referring also now to FIG. 9, there is shown device 10 and vessels 300 and 200 approximately as they might appear where the fistula has been formed. Two sutures 400 are shown on opposite sides of device 10 and vessel 300, which may project slightly into vessel 200, with sutures 400 securing the vessels and device together. In a practical implementation strategy, vessel 300 is a vein, such that opening 304 is formed in a cut end of the vein. Vessel 200 is an artery such that opening 204 is formed in the side of artery 200. With blood flow communication established between first and second vessels 300 and 200, helical flow in blood passed through lumen 20 may be induced via vanes 28, 30 and 32.

Figure 10:
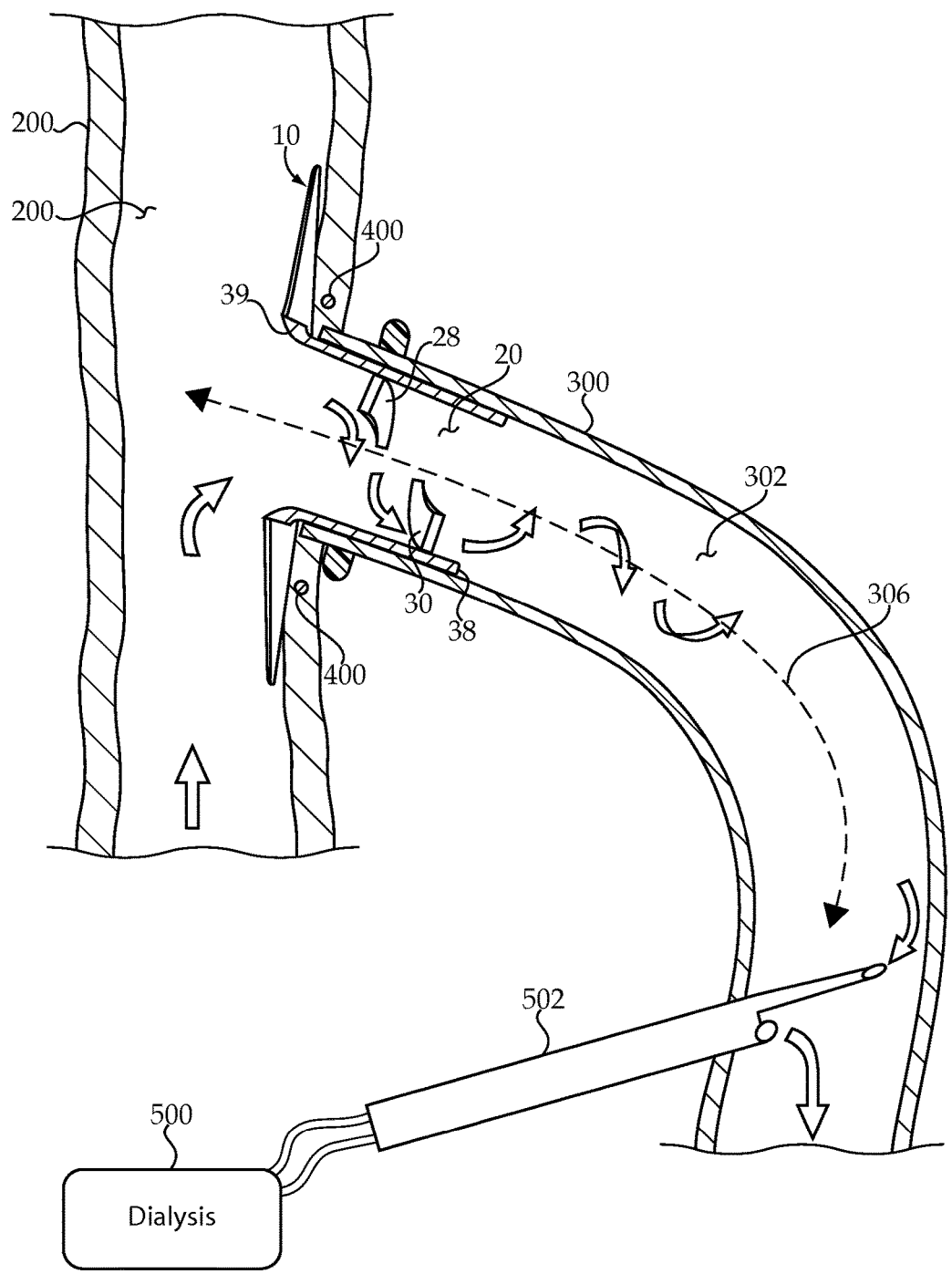
FIG. 10 is a diagrammatic view at one stage of another procedure, according to one embodiment.

Referring now to FIG. 10, it will be recalled that a practical application of fistula formation is in facilitating hemodialysis. In FIG. 10, a dialysis mechanism 500 is shown coupled with a catheter mechanism 502 that has been positioned within vessel 300 to both receive and return blood for conventional dialysis treatment. Catheter mechanism 502 is illustrated as having both an outflow lumen/port and an inflow lumen/port within the same device body. In other instances separate withdrawal and return needles or the like can be used. Also shown in FIG. 10 are arrows illustrating approximate blood flow directions as they might appear where helical flow is induced via vanes 28, 30 and 32, and also where the helical flow persists for some distance downstream of device 10. It should be appreciated that the term helical flow is a descriptive term meaning at least some of the blood in any given section of a blood vessel is traveling in a helical pattern, not necessarily that all of the blood is traveling in a helical pattern. It is in fact likely that a relatively modest extent of helical flow at or close to an inner vessel wall is likely all that is needed to glean the benefits contemplated herein. Circumferential flow components about axis 306 of vessel lumen 302 are seen some distance downstream of device 10. It has been discovered that helical outflow may persist at least several device lengths downstream, potentially several centimeters, and is considered to provide advantages over known fistula devices that do not induce such flow, promoting long-term fistula patency. With at least some circumferential velocity components to the blood flow, in other words some helical flow, the pattern of blood flow communication between vessels 200 and 300 is believed to have similarities to native blood flow patterns through various parts of the human vasculature. For these reasons, the remodeling processes necessary to support relatively high pressure drops from an artery to a vein and high flow rates needed for efficient hemodialysis, are expected to have greater likelihood of successfully occurring than with conventional techniques. Neointimal hyperplasia or NIH as described above may also be less likely.

The present description is for illustrative purposes only, and should not be construed to narrow the breadth of the present disclosure in any way. Thus, those skilled in the art will appreciate that various modifications might be made to the presently disclosed embodiments without departing from the full and fair scope and spirit of the present disclosure.

Other aspects, features and advantages will be apparent upon an examination of the attached drawings and appended claims.

What is claimed is:

1. A method of connecting blood vessels in a patient comprising the steps of:
    sliding a first end of a tubular body in a device for forming a fistula into an opening in the end of a first vessel so as to fluidly connect the first vessel with a lumen in the tubular body;
    sliding a flange attached to a second end of the tubular body into an opening in the side of a second vessel so as to fluidly connect the second vessel with the lumen;
    establishing blood flow communication between the first vessel and the second vessel via the fluid connections of the first and second vessels with the lumen; and
    inducing helical flow in blood passed through the lumen via a vane projecting into the lumen;
    wherein the step of sliding the first end further includes advancing the first end into an opening in a cut end of a vein, and wherein the step of sliding the flange includes inserting the flange into a slit in the side of an artery;
    securing the first vessel upon the tubular body via a resilient band that is out of contact with the tubular body; and
    wherein the step of securing further includes rolling the resilient band from a position in contact with the tubular body over the cut end of the vein so as to secure the vein to the tubular body once the first end is received therein.

* * * * *